(12) United States Patent
Kuslich

(10) Patent No.: US 6,199,551 B1
(45) Date of Patent: Mar. 13, 2001

(54) APPARATUS FOR ESTABLISHING AND MAINTAINING A POSITIVE ATMOSPHERIC PRESSURE SURGICAL FIELD

(75) Inventor: Stephen D. Kuslich, Stillwater, MN (US)

(73) Assignee: Spineology, Inc., Stillwater, MN (US)

( * ) Notice: Subject to any disclaimer, the term of this patent is extended or adjusted under 35 U.S.C. 154(b) by 0 days.

(21) Appl. No.: 09/207,729

(22) Filed: Dec. 8, 1998

(51) Int. Cl.[7] .................................................. A61G 10/00
(52) U.S. Cl. .............................. 128/205.26; 128/202.12; 128/202.16; 128/849; 604/290; 600/21
(58) Field of Search ..................... 128/205.26, 202.12, 128/202.16, 845, 856, 849; 604/290; 600/29

(56) References Cited

U.S. PATENT DOCUMENTS

| 2,385,683 | * | 9/1945 | Burton | 128/202.12 |
| 2,700,384 | * | 1/1955 | Ivory | 128/202.12 |
| 3,094,983 | * | 6/1963 | Macleod | 601/9 |
| 4,467,798 | * | 8/1984 | Saxon et al. | 128/202.12 |
| 4,550,713 | | 11/1985 | Hyman . | |
| 4,893,615 | * | 1/1990 | Khabirova | 128/202.12 |
| 5,060,644 | * | 10/1991 | Loori | 128/202.12 |
| 5,109,837 | | 5/1992 | Gamow et al. . | |
| 5,316,541 | * | 5/1994 | Fischer | 600/21 |
| 5,327,904 | * | 7/1994 | Hannum | 128/202.12 |
| 5,398,678 | | 3/1995 | Gamow et al. . | |
| 5,467,764 | * | 11/1995 | Gamow | 128/202.12 |
| 5,503,143 | * | 4/1996 | Marion et al. | 128/202.12 |
| 5,797,403 | * | 8/1998 | DiLorenzo | 128/856 |
| 5,848,998 | * | 12/1998 | Marasco, Jr. | 604/290 |
| 5,975,081 | * | 11/1999 | Hood et al. | 128/845 |

\* cited by examiner

Primary Examiner—John G. Weiss
Assistant Examiner—V. Srivastava
(74) Attorney, Agent, or Firm—Vidas, Arrett & Steinkrau

(57) ABSTRACT

An apparatus for enclosing a portion of a patient in need of surgery to define an enclosure in which a positive air pressure is introduced to decrease blood loss during surgery. This apparatus may be used to provide a generally sterile field and to decrease blood loss during surgery.

7 Claims, 4 Drawing Sheets

APPARATUS FOR ESTABLISHING AND MAINTAINING A POSITIVE ATMOSPHERIC PRESSURE SURGICAL FIELD

BACKGROUND OF THE INVENTION

1. Field of the Invention

This invention relates to a surgical apparatus which functions during surgical procedures to reduce blood loss that would otherwise normally occur from cut or similarly exposed blood vessels, especially veins and capillaries by imposing upon these capillaries an amount of air pressure sufficient to interfere with the passage of blood through and out of the damaged blood vessels.

2. Description of the Related Art

Currently there exist several techniques and apparatuses which are used to aid in decreasing blood loss during surgical procedures. Primary of these are the bulky and intrusive direct pressure means which usually consist of the application of direct physical pressure upon a wound by the surgeon's hand, gauze, or bandage. In addition techniques exist which provide for the cauterization and ligation of blood vessels.

One such means for applying direct pressure to a wound is known as a M.A.S.T. suit which is most commonly used as a military anti-shock trouser. This device is essentially an inflatable trouser which is most commonly placed over the lower two-thirds of a person. Once in place, the trouser is inflated to a predetermined pressure thereby preventing further blood loss from the wounded member and squeezing blood from the peripheral to the central blood system. Unlike the present invention, the M.A.S.T. suit does not provide for the additional ability to access the wound site by a surgeon or other medical personnel. Before the wound can be further accessed for proper dressing or additional medical procedures the anti-shock trouser must be deflated and removed, thus allowing the bleeding to begin anew.

Several well-known methods exist for establishing a chamber that increases the barometric pressure within the chamber. Such chambers, most notably the various hyperbaric chambers as disclosed by Gamow et al. in U.S. Pat. Nos. 5,109,837; 5,467,764 and 5,398,678, create a generally short term sealed high pressure environment suitable for an individual to sleep in or to alleviate the conditions associated with high altitude environments commonly known as mountain sickness. In these chambers, the entire patient is inside the chamber and the increased pressure, being system-wide has no effect on bleeding control. U.S. Pat. No. 4,550,713 discloses a system for preventing deformation of an eye when incised that includes a ring sewn to the eye and a means to raise the pressure at the eye to counteract the pressure within the eye.

The present invention overcomes the shortcomings of these prior art methods by providing increased air pressure to be placed on the wound site of the individual contained in an enclosure or around the entire surgical suite, by means of a gas pressure field which limits blood loss. Furthermore, the present invention provides for a means to regulate and provide a variety of gases at various flow rates and mixtures. Also the present invention provides for a means to allow individuals to readily pass into and out of the enclosure.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

In accordance with the present invention a positive pressure surgical field for use in reducing bleeding during surgical procedures provides an enclosure having an opening which allows the enclosure to be placed over or around a wound site. In the preferred embodiment the enclosure is self-supporting and is constructed out of transparent plastic.

The enclosure is filled with a positive flow of gas. The resulting flow results in the interior of the enclosure having a higher pressure relative to the outside standard room air pressure. This enclosed positive pressure field is applied to an operation site via the aforementioned opening. In one embodiment, the opening may be of sufficient size to allow nearly the entire patient to be exposed to the positive pressure field, with the exception of the head and upper chest of the patient. In this preferred embodiment the surgical team may be enclosed in the field as well, to allow for easier access to the patient. In an alternate embodiment, the enclosure is of a size sufficient to allow only a small area of the patient to be exposed to the positive pressure field. In such an embodiment the surgeons access the operation site through several openings in the sides of the enclosure.

Since the patient is breathing air at a pressure lower than that within the positive pressure surgical field, pressure is applied to the blood vessels, collapsing or partially collapsing these vessels to limit oozing blood loss. The pressure may be adjusted until the bleeding ceases.

Both forms of the invention may be readily transported and used outside of surgical theaters to provide the benefits of the invention, as well as providing a generally sterile environment. Thus, bleeding and contamination may be controlled in the field by the use of the enclosures of the invention.

BRIEF DESCRIPTION OF THE DRAWINGS

A detailed description of the invention is hereafter described with specific references being made to the drawings which.

DESCRIPTION OF THE PREFERRED EMBODIMENTS

The enclosed positive pressure surgical field as described herein is put into place by constructing a sealed plastic enclosure 10 of appropriate size to cover that area of the patient's body 12 which is to be exposed through surgical means. The enclosure 10 may have multiple embodiments having varying sizes and shapes to allow its use under a variety of surgical conditions.

Figure 1:
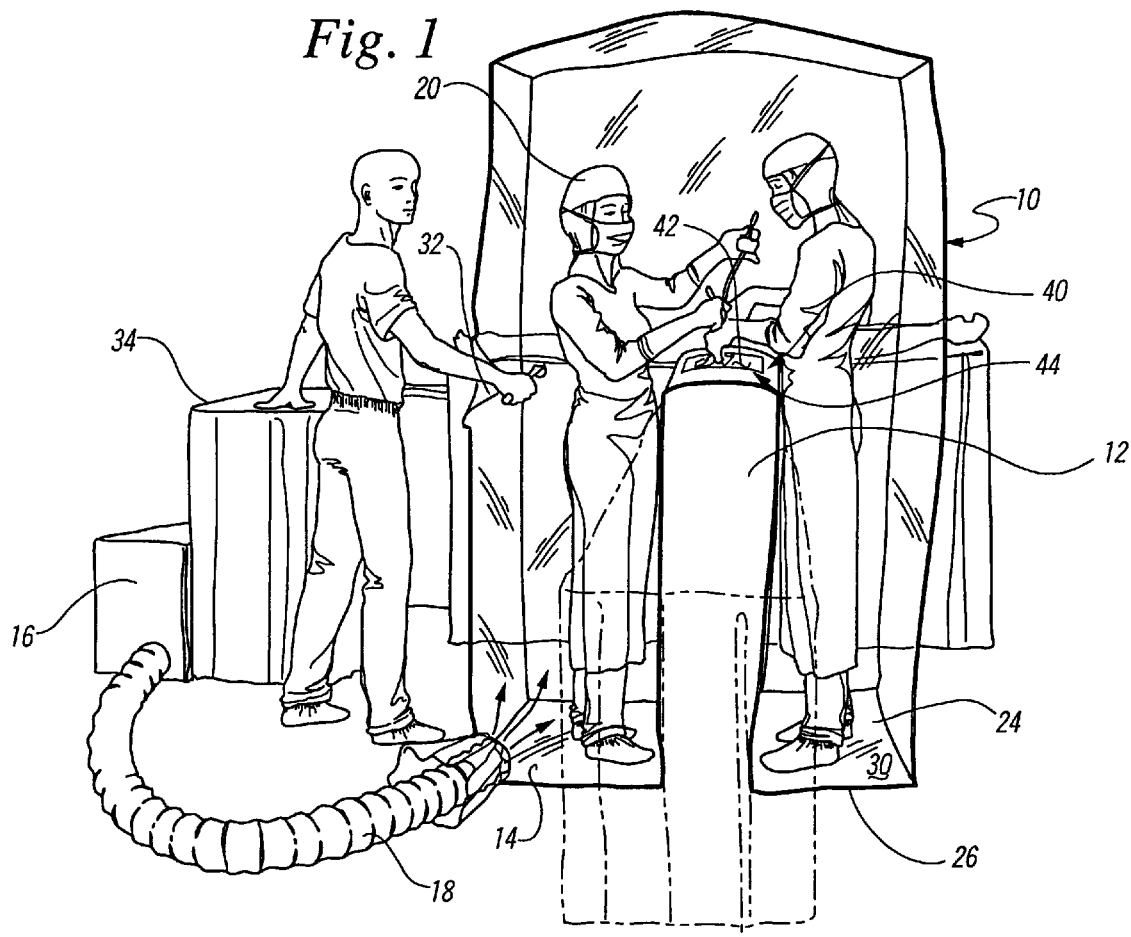
FIG. 1 shows an embodiment of the invention in which the surgeons are within the enclosure, and the air compressor, connective tubing and enclosure wall openings.

FIG. 1 shows an embodiment of the invention wherein a large area of the patient's body 12 is exposed to the air pressure within the enclosure 10. This embodiment is large enough to allow the attending surgeons 20 to directly access the operation site 40 by standing within the enclosure 10. The increased air pressure does not interfere with their surgery and the increase in air pressure is so low that it has little effect on them, especially since they breathe air at the same pressure.

Figure 2:
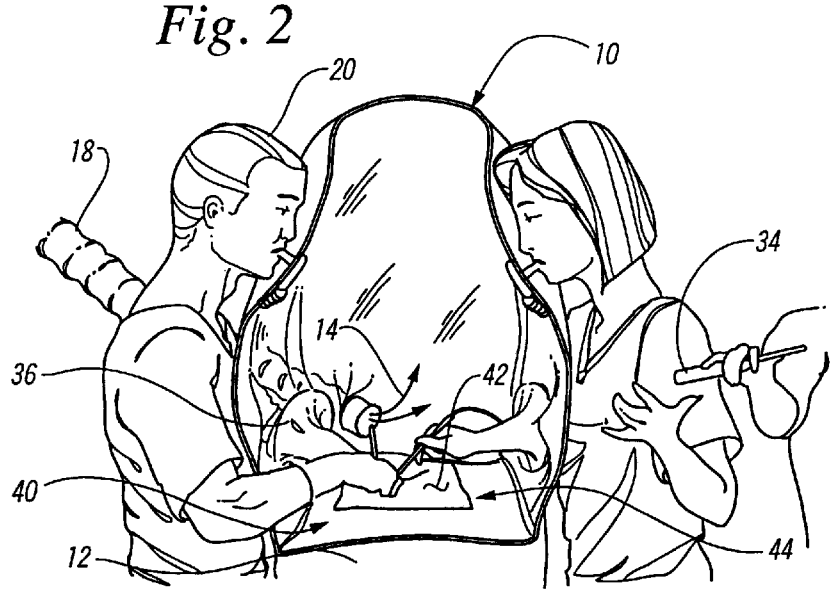
FIG. 2 shows an embodiment of the invention wherein only the area of the patient's body that is being exposed by surgical means is placed within the enclosure and the surgeons operate through openings in the enclosure surface.

FIG. 2 shows a small scale application of the invention wherein only that portion of the patient's body 12 which is being operated upon is placed within the field. This form of the invention requires a generally air-tight seal around the wound site 40, such as an abdomen, and the surgeons 20 gain access through portals 36. The portals 36 may be gloves as in a glove-box or may be a sealing system wherein the surgeon may pass an arm through a sealed portal that maintains the seal around the forearm of the surgeon. Note that if an arm is the site of surgery, that the air-tight seal could be around the upper arm, and not at the wound site.

In either embodiment disclosed, once the enclosure 10 is in place, a volume of gas (represented as three solid arrows 14) is injected into the enclosure 10 from an air producing mechanism 16. Gas produced by this mechanism travels to the enclosure 10 through a transport tube or pipe 18. Such a mechanism may be an air compressor, or air blower but need not be limited to these two examples. Generally, operating rooms often have sophisticated air supply systems which may simply be tapped to supply air to the enclosure 10. Note that "gas" as it is used in this disclosure is intended to mean standard room air. However, the inventor recognizes that a wide variety of neutral gases could be used to fill the enclosure 10 and establish the positive pressure field described. Therefore, air should not be seen as the exclusive medium to be used for this aspect of the invention.

Gas fills the enclosure 10 to a pressure determined by the attending surgeons 20. The desired pressure will coincide with a positive pressure value in comparison with the air pressure supplied to the patient. This positive pressure field when in contact with exposed bloods vessel will result in the imposition of a pressure barrier upon the exposed vessels. Such a barrier will prevent capillaries and veins from losing bodily fluids such as blood during the surgical procedure. Benefits may be achieved with as little as a 5 mm Hg increase in pressure. A typical range of pressure increases that may be used to reduce bleeding and oozing would be between about 5 and about 20 mm of pressure.

Figure 3:
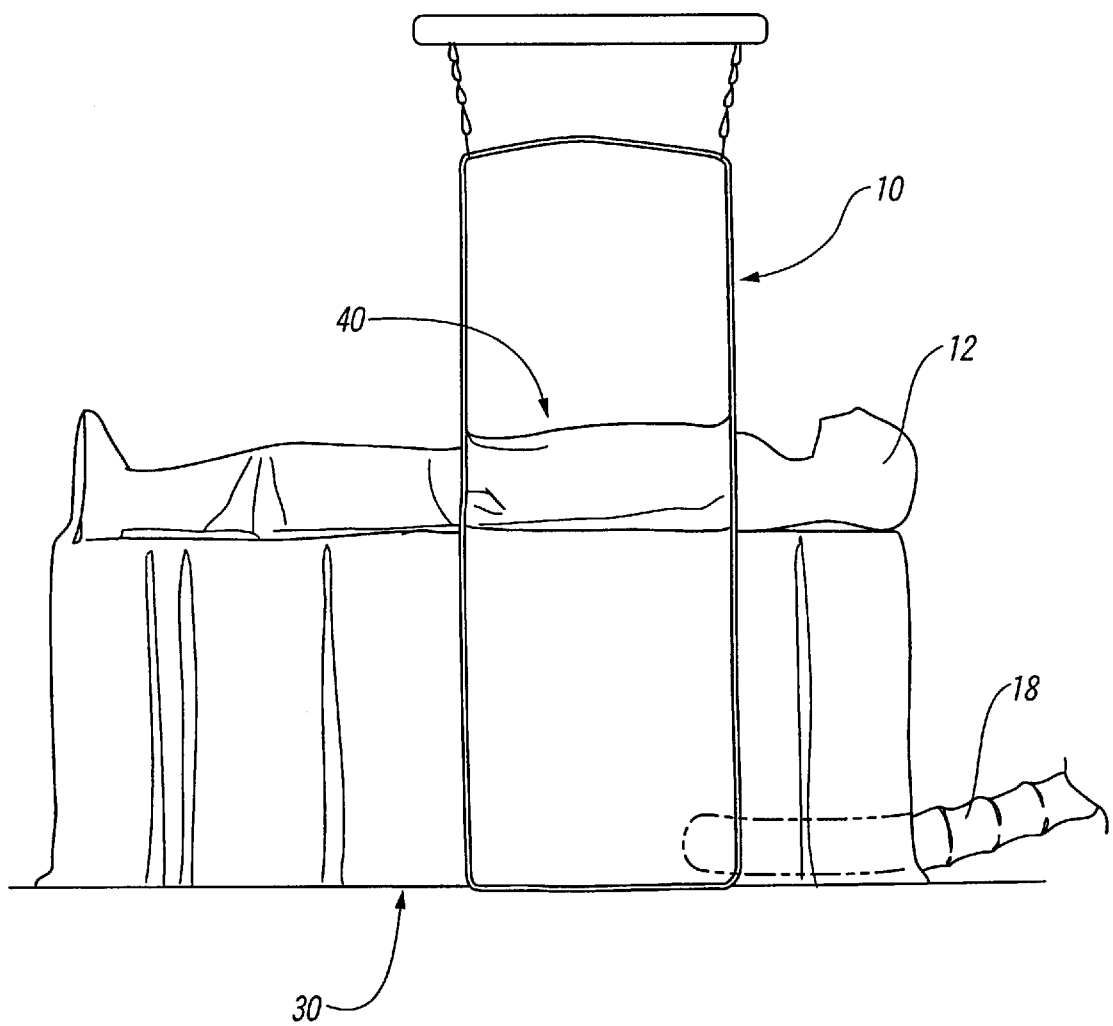
FIG. 3 shows a side view of the invention of FIG. 1 to show that the patient's entire body is not within the enclosure.
Figure 4:
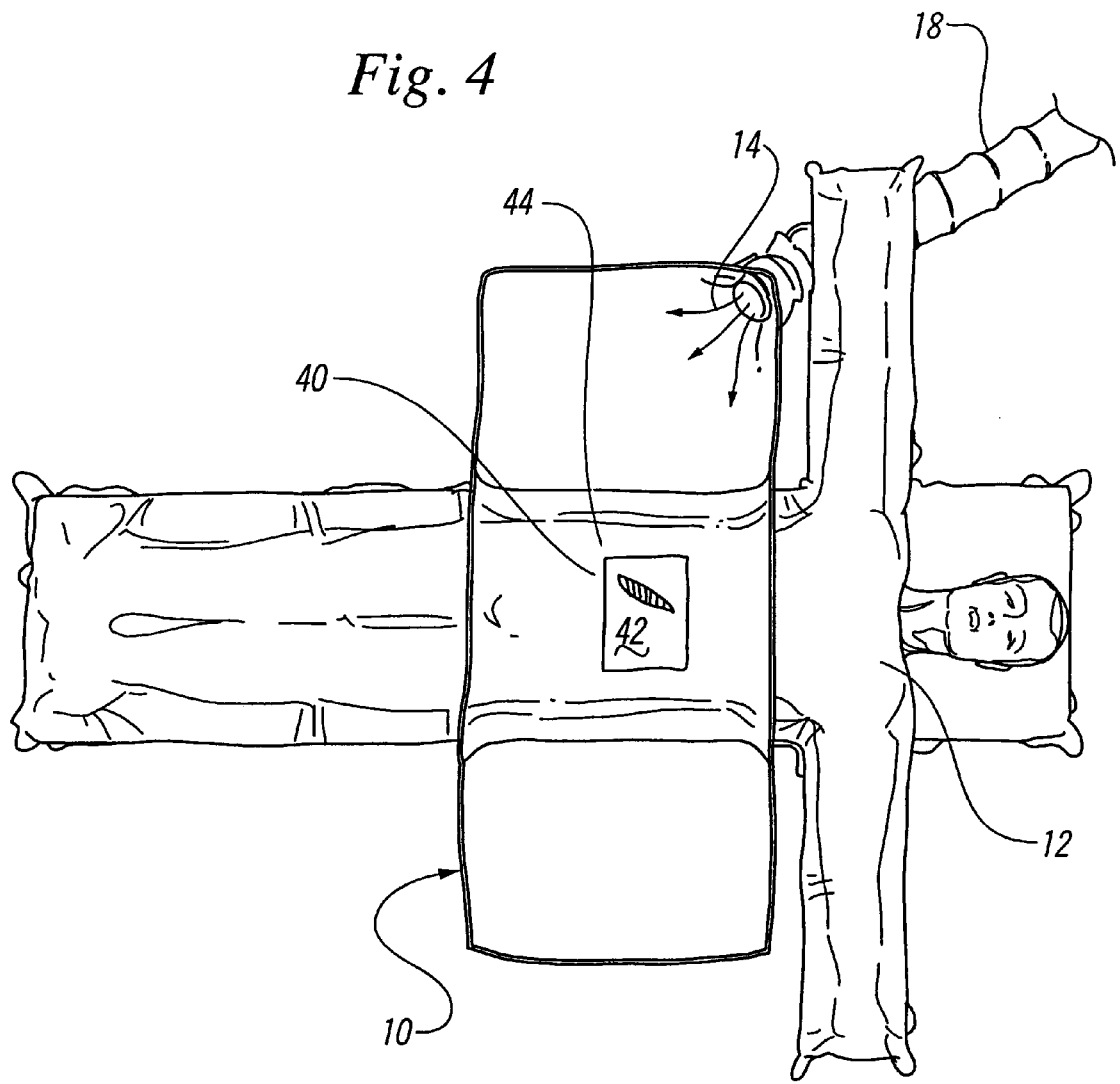
FIG. 4 is a top view of the enclosure of FIG. 1 showing the patient's body relative to the enclosure the surgeons would occupy.

The embodiment illustrated in FIG. 1 allows for easier access to the patient by the surgical team. The patient's head, which is not visible in the figure, is excluded from the field in this embodiment. The patient's head and upper chest is not placed in the field, as best shown in FIGS. 3 and 4, due to the need to have the patient breathing lower pressure air in order for the higher pressure of the field to be effective. In order for the patient to maintain proper breathing when a portion of his body is subjected to elevated pressure to control bleeding, the upper thoracic area of the patient and head needs to be at ambient pressure. The entire patient may not be within the enclosure as the effects of the invention require a difference in pressure at the surgical site relative to the patient's breathing pressure. The patient cannot simply be within the enclosure and be fed air at a lower pressure since his lungs would not lift.

In this embodiment, the enclosure 10 is large enough to allow the surgeons 20 to operate entirely within the enclosure 10 and positive pressure field. Note that in the embodiment of FIG. 1, the operating room floor 30 is adjacent opening 24 and a mechanical seal may be added at the edges 26 of the opening 24 to maintain the pressure seal at the floor. Alternatively, the surgeons may simply stand on top of part of the enclosure 10 such that they are entirely within the enclosure bag without direct contact with the operating room floor.

An additional benefit of the present invention is the added flexibility provided to the surgeons by being able to regulate the type of gas introduced to the enclosure 10 in addition to the gas pressure, humidity, and other standard atmospheric conditions within the surgical field. More specifically, the air producing mechanism 16 may have the added ability to contain, regulate, and emit a variety of gases in addition to oxygen. For instance, by introducing predominately $CO_2$ gas into the enclosure 10 instead of a standard oxygen and nitrogen mixture, the surgeons 20 are much more able to prevent the occurrence of air embolisms which are known to be a life threatening affliction which can affect patients in many surgical procedures. Obviously, when a $CO_2$ atmosphere of this type is introduced to the embodiment shown in FIG. 1 the surgeons 20 would need to be fed breathable air from an outside source. The atmospheric control is achieved through the air producing mechanism 16 which maintains desired pressures by inflow and outflow control, allows ventilation and allows adjustment of any parameter of the atmosphere within the enclosure, as is commonly performed by standard operating room ventilation systems. Any such device may be either simply hooked up to the enclosure or modified to work with the apparatus of this invention.

As shown in FIGS. 1 and 4–7, the surgeons 20 within the enclosure 10 operate through opening 42 to reach the surgical site 40. The edges 44 of the opening 42 form a generally air tight seal against the patient's body. The seal may be by simple air pressure or may be increased by the addition of an adhesive, shown as layer 46 in FIG. 7. Such an adhesive 46 may be applied by a variety of mechanisms and may be embodied in a number of different forms including pre-application of the adhesive to the edges 44 with activation occurring upon removal of a release tape. In all forms of the invention, portals are required for the surgeons and for passing instruments and the like in and out of the enclosure. The portals are designed to minimize pressure changes such that a temporary opening may be made and resealed.

Figure 5:
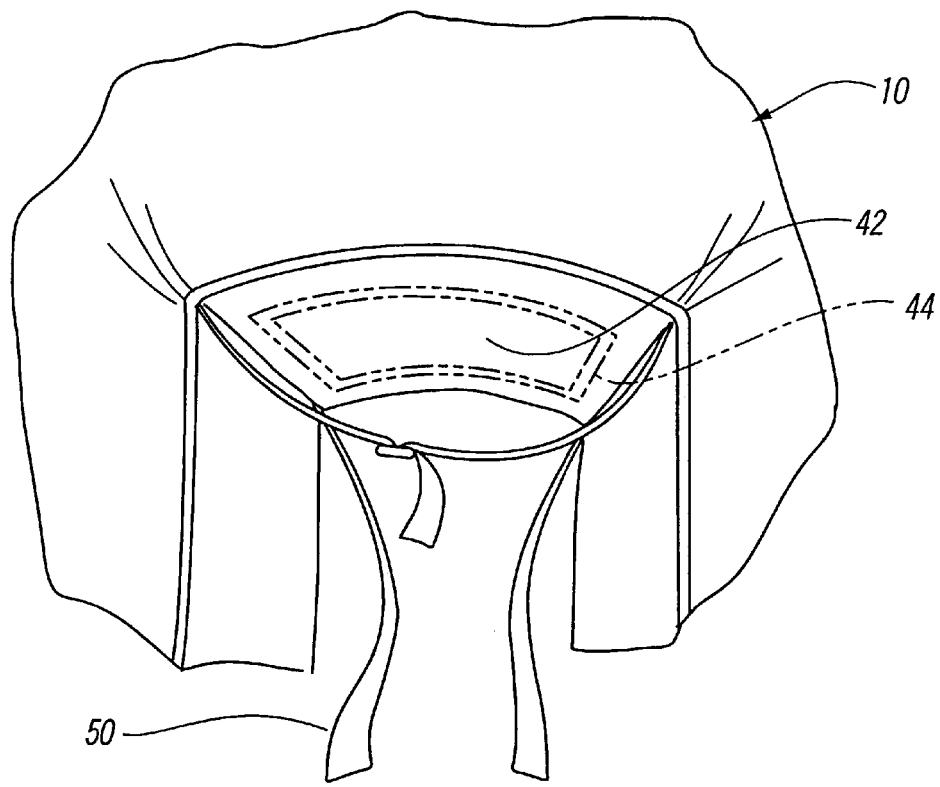
FIG. 5 shows a partial end view of the enclosure of FIG. 1 to detail how the enclosure may be secured at the surgical site.
Figure 7:
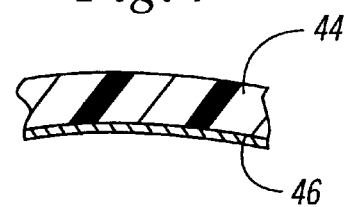
FIG. 7 is a cross-sectional view of the window of the enclosure through line 7—7 of FIG. 6.
Figure 6:
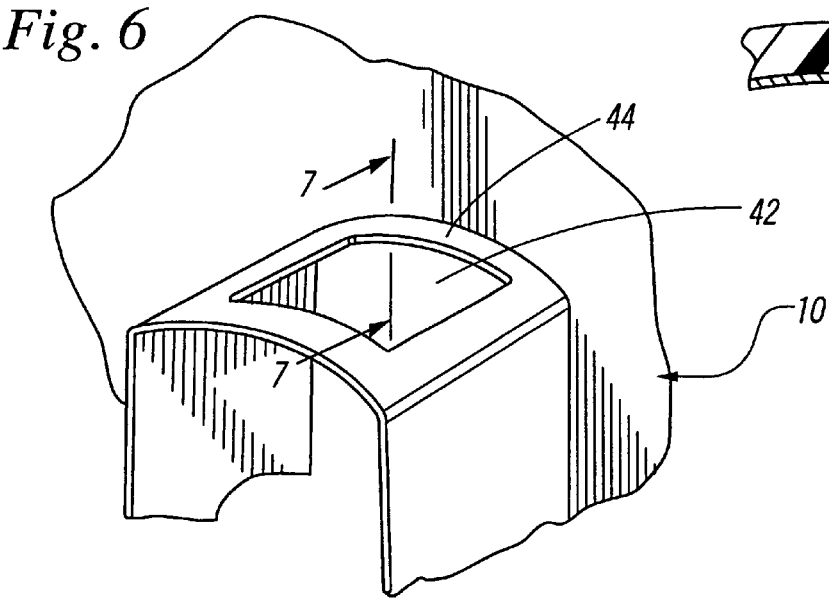
FIG. 6 shows a view of the enclosure of FIG. 5 showing the window through which the surgeons may operate.

As shown in FIG. 5, the enclosure 10 may also include a tie mechanism 50 attached to the enclosure 10 adjacent to the edges 44 and which may pass underneath the patient's body 12. These ties 50 prevent the enclosure 10 from ballooning away from the surgical site 40 during initial inflation of the enclosure 10.

In FIG. 2, the area of the patient's body which is to be operated on is exposed to the field by opening 42. As in FIG. 1, the opening 42 can vary in size depending on the type and magnitude of the operation. An adhesive may be used to secure the enclosure 10 to the patient's skin. In addition, or in the alternative, the edges 44 of the opening 42 may be weighted to decrease any tendency of the enclosure 10 to lift from the site. Furthermore the smaller embodiment of FIG. 2 may also include a form of the tie-off mechanism 50 as illustrated in FIG. 5.

To maintain the level of pressure within the enclosure 10 which the attending surgeons 20 have decided upon, the enclosure 10 will require a number of seals at the various interface points it has with the outside environment. FIG. 1 shows that the enclosure 10 has a series of self supporting walls of plastic. At the juncture of the surgical suite's floor 30 and the enclosure 10 opening 24, the enclosure's own weight may act to roughly seal the enclosure 10 to the floor. However, there could be a variety of embodiments which have a more active form of seal such as an adhesive or a weighted lower edge 26. In addition, as previously mentioned, the surgeons may stand on the plastic of the enclosure 10 and thus be entirely within the enclosure 10. Furthermore, as can be seen in FIG. 2, the embodiment may have a bag-like enclosure 10 and lack the need for a floor seal. Other areas of the enclosure 10 may benefit from a seal, such as opening 42 in the embodiment of FIG. 2 which provides for access to the patient 12.

In order to facilitate the various instruments and objects that must be used during a surgical procedure, the enclosure 10 has several openings or windows 32 which allow surgical tools 34 to be passed into and out of the enclosure 10 with minimal loss of air pressure. In the disclosed embodiment these openings 32 consist essentially of a hole in the wall of the enclosure 10 which are covered by a moveable portion of similarly sealed material. These openings are normally covered by this material when in their closed position, but are capable of being opened by simply pulling the covering material away. Upon completion of the passage of a surgical tool, the cover can be quickly replaced, thus minimizing a pressure loss within the field.

FIG. 2 illustrates a second type of portal 36 which may be included in various embodiments of the invention. They may simply provide a seal around the surgeons' arm or may provide a glove-box arrangement.

Note that the invention may also be used to form a mobile sterile operating theater for remote areas that do not have acceptable medical facilities. The enclosure 10 provides the added benefit of forming a generally sterile and isolated theater in which to operate, with the positive pressure therewithin helping to maintain the integrity of the field from outside contaminants.

This completes the description of the preferred and alternate embodiments of the invention. Those skilled in the art may recognize other equivalents to the specific embodiment described herein which equivalents are intended to be encompassed by the claims attached hereto.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

What is claimed is:

1. An apparatus for establishing and maintaining a positive atmospheric pressure surgical field for use in reducing bleeding during surgical procedures comprising:

(a) an enclosure constructed and arranged to define a chamber, the chamber sized to permit at least one member of a surgical team to be completely contained therein, the chamber having an opening to permit access to a surgical site of a patient from within the enclosure, the opening constructed and arranged to surround and form an air-tight seal about the surgical site of the patient thereby enclosing the surgical site within the chamber while excluding the rest of the patient from the chamber; and (b) a gas mechanism for delivering gas to said chamber to provide a positive gas pressure therewithin, said gas mechanism being capable of delivering sufficient gas volume to said chamber to cause said chamber to fill with said gas and establish an air pressure field within the enclosure which is greater than the air pressure outside the enclosure, the positive gas pressure providing the surgical site with an air pressure sufficient to inhibit bleeding and which is greater than that which the patient is exposed to outside the enclosure, said gas mechanism providing an exchange of air to maintain the concentration of gases as desired.

2. The apparatus of claim 1 wherein the gas mechanism for delivering gas provides the ability to control gas flow rate in and out of said enclosure.

3. The enclosure of claim 1 wherein said enclosure is constructed out of transparent plastic.

4. The enclosure of claim 1 wherein the enclosure has a series of closeable openings to allow passage of the at least one member of the surgical team into and out of said enclosure.

5. The apparatus of claim 2 wherein said gas mechanism provides breathable gas to a surgical team within said enclosure and provides a carbon dioxide environment at the patient's surgical site.

6. The apparatus of claim 1 wherein the gas mechanism for delivering gas provides the ability to control gas type fn said enclosure.

7. A method for establishing and maintaining a positive pressure surgical field for use in reducing bleeding during surgical procedures comprising the steps of:

(a) encompassing the area of the patient which is to be operated upon and at least one member of a surgical team with a generally air-tight enclosure;

(b) filling said enclosure with an amount of gas sufficient to create a relative air pressure inside said enclosure greater than that which is outside said enclosure;

(c) injecting gas into said enclosure to maintain the required pressure;

(d) exposing the area of the patient to be operated upon to the air pressure within said enclosure by means of an opening in the enclosure, the portion of the patient not being operated upon being exposed to the air pressure outside of the enclosure; and (e) adjusting the air pressure within the enclosure until bleeding caused by surgical incisions is reduced.

* * * * *

UNITED STATES PATENT AND TRADEMARK OFFICE
CERTIFICATE OF CORRECTION

PATENT NO.    : 6,199,551 B1
DATED         : March 13, 2001
INVENTOR(S)   : Stephen D. Kuslich It is certified that error appears in the above-identified patent and that said Letters Patent is hereby corrected as shown below:

Column 6,
Line 36, delete "fn" and insert -- in. --

Signed and Sealed this

Thirteenth Day of November, 2001

Attest:

*Nicholas P. Godici*

NICHOLAS P. GODICI
*Attesting Officer*        *Acting Director of the United States Patent and Trademark Office*